United States Patent
Huang et al.

(10) Patent No.: US 9,267,785 B2
(45) Date of Patent: Feb. 23, 2016

(54) CENTRIFUGAL ANALYSIS SYSTEM AND ANALYSIS METHOD THEREOF

(71) Applicant: LITE-ON TECHNOLOGY CORPORATION, Taipei (TW)

(72) Inventors: Fu-Chun Huang, Taipei County (TW); Cheng Chang Lai, Taipei (TW)

(73) Assignee: Lite-On Technology Corporation, Taipei (TW)

( * ) Notice: Subject to any disclaimer, the term of this patent is extended or adjusted under 35 U.S.C. 154(b) by 0 days.

(21) Appl. No.: 14/497,225

(22) Filed: Sep. 25, 2014

(65) Prior Publication Data

US 2015/0138567 A1    May 21, 2015

Related U.S. Application Data (60) Provisional application No. 61/906,071, filed on Nov. 19, 2013.

(51) Int. Cl.

| | |
|---|---|
| *G01B 11/14* | (2006.01) |
| *B04B 7/08* | (2006.01) |
| *B04B 9/00* | (2006.01) |
| *B01L 3/00* | (2006.01) |
| *G01N 21/07* | (2006.01) |
| *G01N 35/04* | (2006.01) |
| *G01N 35/00* | (2006.01) |

(52) U.S. Cl.
CPC ............. *G01B 11/14* (2013.01); *B01L 3/5027* (2013.01); *B04B 7/08* (2013.01); *B04B 9/00* (2013.01); *G01N 21/07* (2013.01); *G01N 35/04* (2013.01); *B01L 2200/025* (2013.01); *B01L 2200/143* (2013.01); *B01L 2300/0816* (2013.01); *B01L 2400/0406* (2013.01); *B01L 2400/0409* (2013.01); *G01N 35/00069* (2013.01); *G01N 2035/0449* (2013.01); *G01N 2035/0491* (2013.01)

(58) Field of Classification Search
CPC .................................................. G01B 11/14
USPC ............................................................ 356/614
See application file for complete search history.

(56) References Cited

U.S. PATENT DOCUMENTS

| | | | | |
|---|---|---|---|---|
| 3,771,878 A | * | 11/1973 | Molloy .................... | E04H 1/12 356/246 |
| 7,758,810 B2 | * | 7/2010 | Lee ....................... | B01L 3/5027 356/614 |
| 8,242,433 B2 | * | 8/2012 | Kim ................... | B01L 3/502715 250/231.13 |
| 8,289,529 B2 | * | 10/2012 | Hyoudou ............... | G01N 21/07 356/614 |

* cited by examiner

*Primary Examiner* — Roy M Punnoose (57) ABSTRACT

A centrifugal analysis system includes a driving device, a carrying device, a number of cassettes, and an optical sensor device. The carrying device includes a tray disposed on the driving device, a number of limitation mechanisms disposed at the tray. The cassettes are detachably disposed at the tray and respectively and correspond to the limitation mechanisms. When the driving device drives the carrying device to rotate, the optical sensor circularly detects the cassettes in sequence.

15 Claims, 8 Drawing Sheets

CENTRIFUGAL ANALYSIS SYSTEM AND ANALYSIS METHOD THEREOF

CROSS-REFERENCE TO RELATED APPLICATIONS

This application claims the benefit of U.S. Provisional Application No. 61/906,071 filed on Nov. 19, 2013, the contents of which are incorporated herein by reference.

BACKGROUND OF THE INVENTION

1. Field of the Invention

The present disclosure relates to a centrifugal analysis system and an analysis method thereof, and in particular to a centrifugal analysis system having a number of cassettes and an analysis method thereof.

2. Description of the Related Art

In a conventional centrifugal analysis system, only one single cassette is operated in the conventional centrifugal analysis system at a given time, and thus only one kind of specimen in the cassette can be inspected. When another specimen needs to be inspected, another operation is under taken to inspect a new cassette with the new specimen by replacing the previously inspected cassette. In other words, the conventional centrifugal analysis system cannot inspect a number of specimens at the same time, and thus the inspection of a number of specimens takes a lot of time, and is not convenient.

BRIEF SUMMARY OF THE INVENTION

To solve the problems of the prior art, the present disclosure provides a centrifugal analysis system. A number of cassettes can be operated in the centrifugal analysis system, and thus a number of specimens can be inspected at the same time.

The present disclosure provides a centrifugal analysis system including a driving device, a carrying device, a number of cassettes, and an optical sensor device. The carrying device includes a tray disposed at the driving device and a number of limitation mechanisms disposed at the tray. The cassettes are detachably disposed at the tray and correspond to the limitation mechanisms. The optical sensor device is configured to generate a detection beam and to detect the cassettes. When the driving device drives the carrying device to rotate, the optical sensor device detects the cassettes in sequence.

The present disclosure provides an analysis method for a centrifugal analysis system comprising disposing a number of cassettes at a carrying device, wherein each of the cassettes comprises at least one storage groove, and the carrying device comprises a positioning device and a number of detecting holes corresponding to the storage grooves; rotating the carrying device by a driving device; detecting the positioning device and the storage grooves in sequence by an optical sensor device, and generating a number of received signals in sequence; designating one of the received signals as a position signal; and designating that N received signals following the position signal respectively correspond to the storage grooves in sequence.

The present disclosure also provides an analysis method for a centrifugal analysis system comprising disposing a number of cassettes at a carrying device, wherein each of the cassettes comprises at least one storage groove, and the carrying device comprises a positioning device and a number of detecting holes corresponding to the storage grooves; rotating the carrying device by a driving device; detecting the positioning device and the storage grooves in sequence by an optical sensor device, and generating a position signal and a number of inspection signals in sequence; and designating that the inspection signals following the position signal respectively correspond to the storage grooves in sequence.

In conclusion, the centrifugal analysis system of the present disclosure includes a number of cassettes with different specimens. The specimens can be inspected by a single inspection process at the same time. Moreover, the cassettes are detachably disposed at the carrying device via limitation mechanisms and/or retaining mechanisms.

BRIEF DESCRIPTION OF THE DRAWINGS

The invention can be more fully understood by reading the subsequent detailed description and examples with references made to the accompanying drawings, wherein.

DETAILED DESCRIPTION OF THE INVENTION

Figure 1:
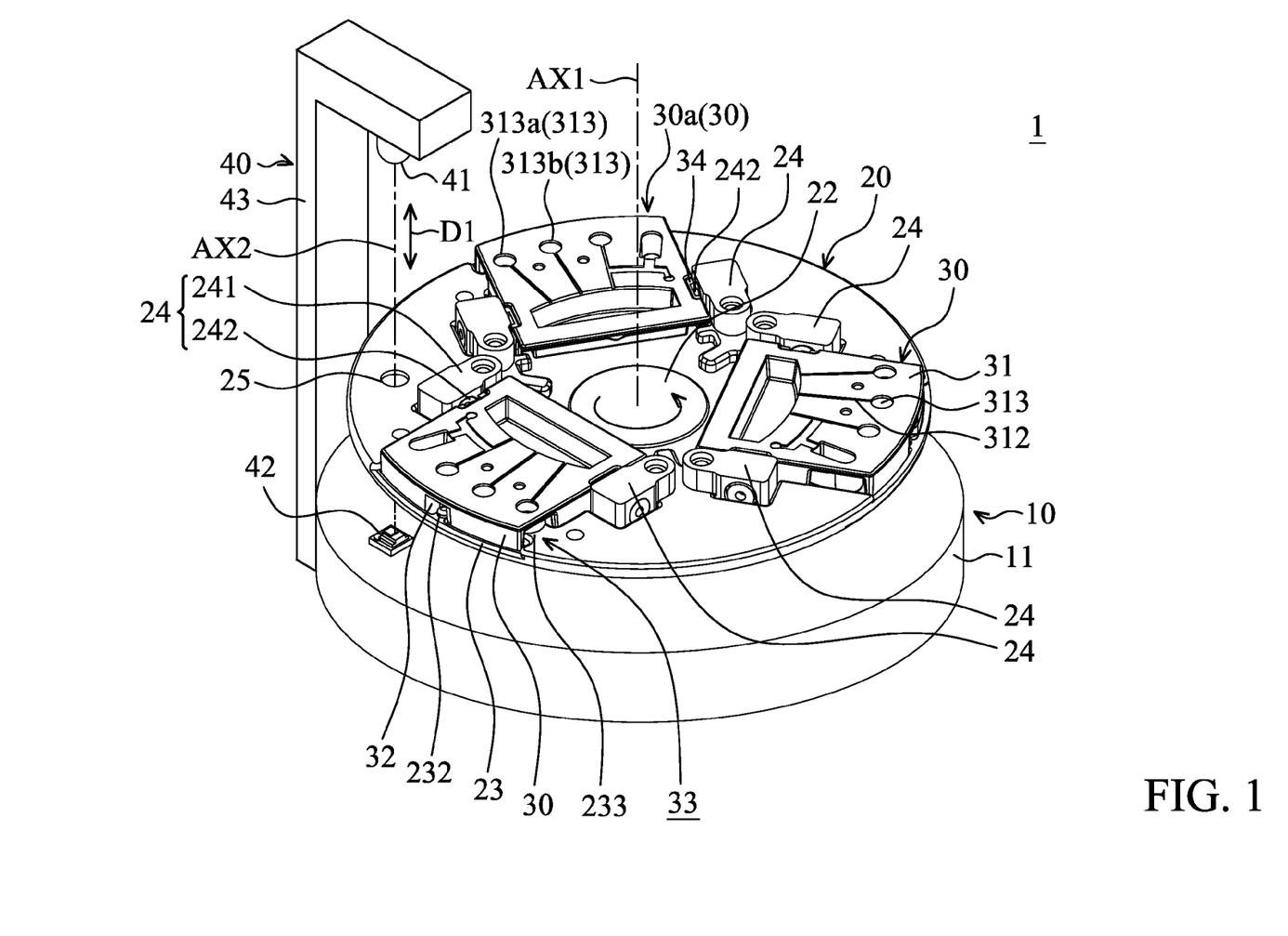
FIG. 1 is a perspective view of a centrifugal analysis system in accordance with a first embodiment of the present disclosure.
Figure 2:
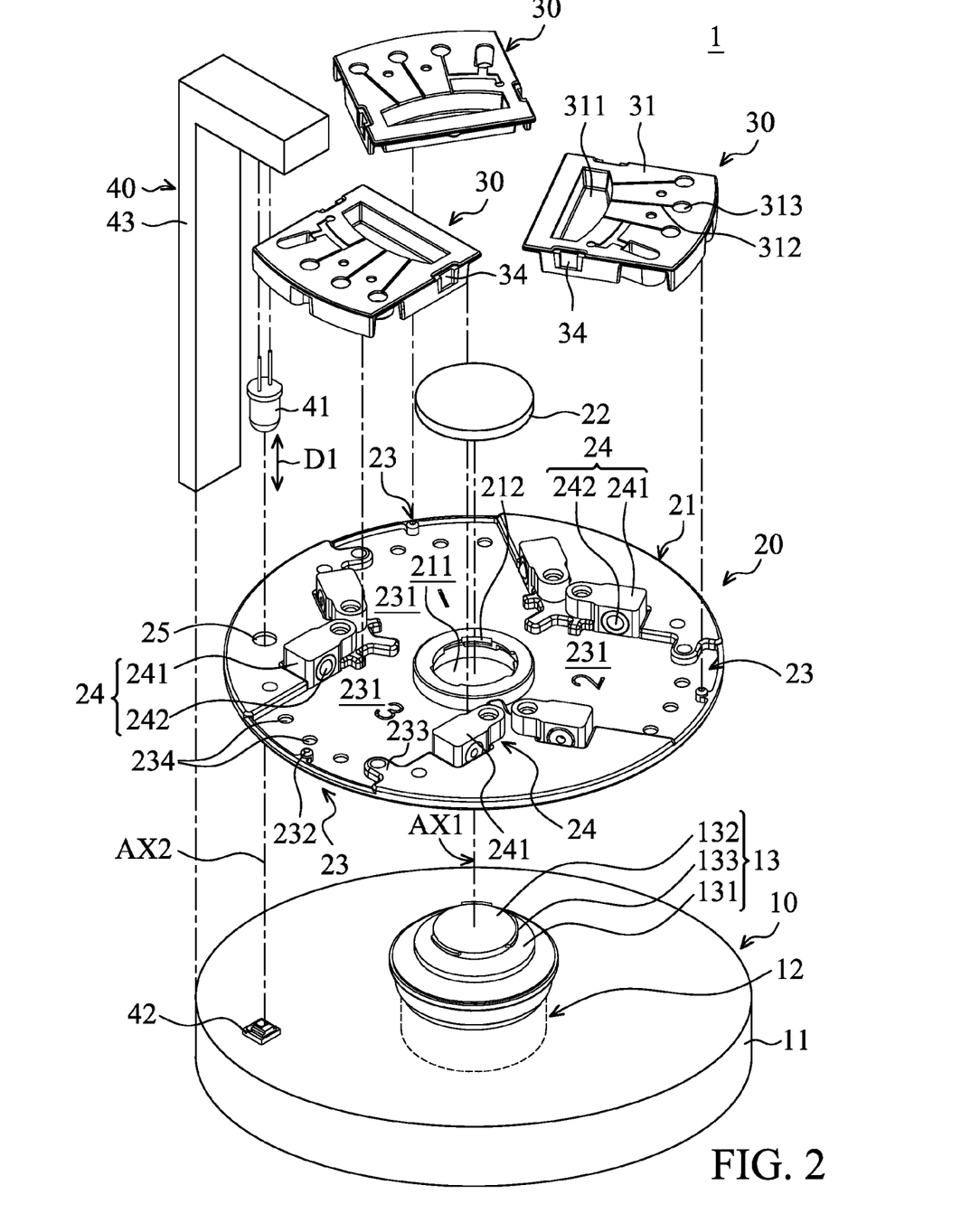
FIG. 2 is an exploded view of the centrifugal analysis system in accordance with the first embodiment of the present disclosure.
Figure 3:
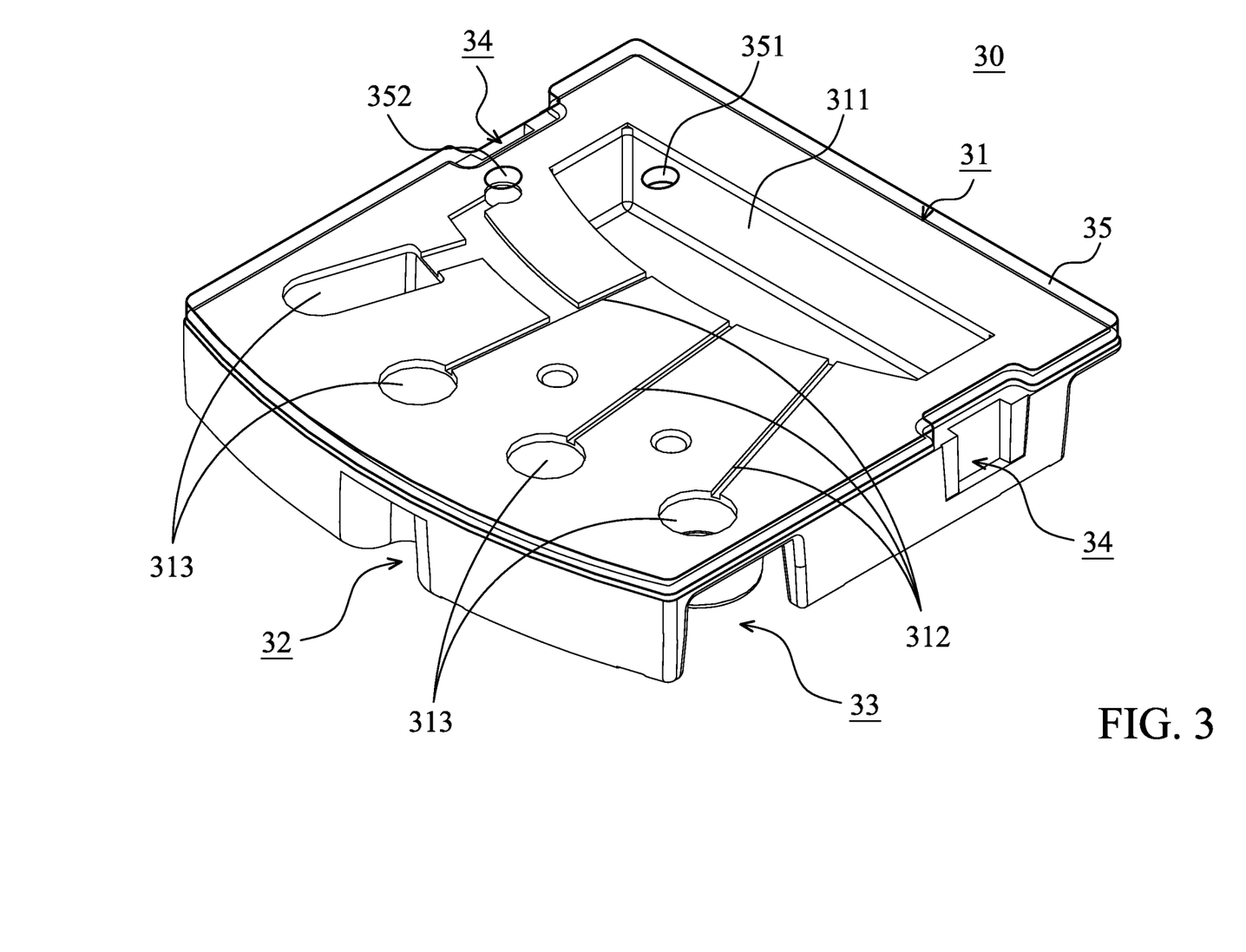
FIG. 3 is a perspective view of a cassette in accordance with the present disclosure.

FIG. 1 is a perspective view of a centrifugal analysis system 1 in accordance with a first embodiment of the present disclosure. FIG. 2 is an exploded view of the centrifugal analysis system 1 in accordance with the first embodiment of the present disclosure. FIG. 3 is a perspective view of a cassette 30 in accordance with the present disclosure. In some embodiments, the centrifugal analysis system 1 is applied to the chemical, medical or biosensor arts.

The centrifugal analysis system 1 includes a driving device 10, a carrying device 20, a number of cassettes 30, and an optical sensor device 40. The driving device 10 is configured to rotate the carrying device 20, and the carrying device 20 is configured to carry the cassettes 30. When the driving device 10 drives the carrying device 20 to rotate, the cassettes 30 are rotated relative to the driving device 10. The optical sensor device 40 is configured to inspect the specimens in each of the rotating cassettes 30 in sequence.

The driving device 10 includes a base 11, a motor 12, and a rotation element 13. The motor 12 is disposed at the base 11. In the embodiment, the motor 12 is a stepper motor or a centrifugal motor. The rotation element 13 is disposed at the motor 12. The motor 12 drives the rotation element 13 to rotate around a rotation axis AX1. The rotation element 13 may be a disk structure, and is substantially extended perpendicular to the rotation axis AX1.

The rotation element 13 includes a rotation disk 131, a cylindrical element 132, and a number of fixing protrusions 133. The rotation disk 131 is fixed at the motor 12, and the rotation axis AX1 passes through the center of the rotation disk 131. The rotation disk 131 is configured to support the carrying device 20 and to make the rotation of the carrying device 20 to be stable. The cylindrical element 132 is disposed at the rotation disk 131. The fixing protrusions 133 are annularly arranged at a sidewall of the cylindrical element 132.

The carrying device 20 includes a tray 21, a cover plate 22, a number of limitation mechanisms 23, a number of retaining mechanisms 24, and a positioning device 25. The tray 21 is disposed over the driving device 10. In the embodiment, the tray 21 contacts a top surface of the rotation disk 131. The tray 21 may be a disk structure, and is substantially perpendicular to the rotation axis AX1. The tray 21 has a shaft hole 211 and a number of fixing grooves 212. The shaft hole 211 is located at a center of the tray 21. In the embodiment, the cover plate 22 covers the shaft hole 211 to prevent an object from falling on the motor 12 via the shaft hole 211.

The fixing groove 212 is annularly arranged at a sidewall of the shaft hole 211. When the tray 21 is disposed at the rotation disk 131, the fixing protrusion 133 is retained in the fixing groove 212. Therefore, the carrying device 20 is easily detached from or installed on the driving device 10, and the replacement of the cassettes 30 of the carrying device 20 is convenient.

The limitation mechanisms 23 are disposed at the tray 21, and the cassettes 30 are detachably disposed at the limitation mechanisms 23 and annularly arranged at the tray 21. Moreover, the limitation mechanisms 23 prevent the cassettes 30 disposed at the carrying device 20 from moving on the tray 21. In the embodiment, the limitation mechanisms 23 and the tray 21 are formed as a single piece. The limitation mechanisms 23 are radially and annularly arranged at the tray 21, and around the shaft hole 211. The cassettes 30 and the limitation mechanisms 23 have corresponding fool-proofing mechanisms for each other.

Each of the limitation mechanisms 23 includes a receiving groove 231, a limitation pillar 232, and a first fool-proofing mechanism 233. The receiving groove 231 is extended from an edge of the tray 21 to a central area of the tray 21. The shape of the receiving groove 231 may correspond to the shape of the cassette 30. Therefore, the cassette 30 is prevented from being disposed at the limitation mechanism 23 by an incorrect way. In the embodiment, the receiving grooves 231 are located at the same plane or horizontal plane.

The limitation pillar 232 and the first fool-proofing mechanism 233 are disposed in the receiving groove 231. In the embodiment, the first fool-proofing mechanism 233 is a fool-proofing element 233 protruding from a sidewall of the receiving groove 231. The limitation pillar 232 and the fool-proofing element 233 are substantially perpendicular to the bottom of the receiving groove 231.

As shown in FIGS. 1 and 2, the positioning device 25 is disposed at the tray 21. Each of the limitation mechanisms 23 further includes a number of detecting holes 234. In the embodiment, the detecting holes 234 are located at the bottoms of the receiving grooves 231. Moreover, the detecting holes 234 penetrate the tray 21. The positioning device 25 may be a positioning hole penetrating the tray 21, a reflecting mirror, or a device generating a signal that is different from a single relative to the detecting hole 234. In the embodiment, the positioning device 25 is a positioning hole 25 penetrating the tray 21, for example. The positioning hole 25 and the detecting holes 234 may be located at the same plane or horizontal plane.

In the embodiment, the cassettes 30 are plate structures. Each of the cassettes 30 includes a body 31, a limitation groove 32 and a second fool-proofing mechanism 33. In the embodiment, the second fool-proofing mechanism 33 is a fool-proofing groove 33 hollowed from the sidewall of the body 31. When the cassette 30 is disposed in the receiving groove 231 of the limitation mechanism 23, the fool-proofing element 233 is located in the fool-proofing groove 33, and the limitation pillar 232 is located in the limitation groove 32.

The limitation groove 32 and the limitation pillar 232 are adjacent to an edge of the tray 21 and distant from the rotation axis AX1. Therefore, the oscillation of the cassettes 30 during rotation is reduced by the limitation groove 32 and the limitation pillar 232.

In the embodiment, the fool-proofing groove 33 is disposed at only one of two opposite sides of the cassette 30, and adjacent to a corner of the cassette 30. The fool-proofing element 233 is disposed at only one of two opposite sides of the receiving groove 231, and adjacent to a corner of the receiving groove 231. Therefore, the configuration of the fool-proofing groove 33 and the fool-proofing element 233 prevents the cassette 30 from be disposed in the receiving groove 231 in an incorrect position.

The retaining mechanisms 24 are disposed at the tray 21. When the cassette 30 is disposed at the limitation mechanism 23, the retaining mechanisms 24 claim two opposite sides of the cassette 30. Each of the retaining mechanisms 24 includes a retaining body 241 and a first retaining element 242. The retaining bodies 241 are located at two opposite sides of the receiving groove 231, and fixed at the tray 21. The first retaining element 242 is disposed at the retaining body 241. In the embodiment, two of the retaining elements 242 face each other. The first retaining element 242 may be an elastic element, a ball spring plunger, a hook, or a retaining groove.

Each of the cassettes 30 further includes two second retaining elements 34. The second retaining elements 34 are located at two opposite sides of the body 31. In the embodiment, the fool-proofing groove 33 and one of the second retaining elements are located at the same side of the body 31. The second retaining element 34 may be an elastic element, a ball spring plunger, a hook, or a retaining groove.

The cassette 30 is disposed in the receiving groove 231 along an extension direction D1 perpendicular to the tray 21. The extension direction D1 is parallel to the rotation axis AX1. When the cassette 30 is disposed in the receiving groove 231 of the limitation mechanism 23, the first retaining element 242 and the second retaining element 34 are retained to each other.

By the first retaining element 242 and the second retaining element 34, the cassette 30 is prevented from separating from the tray 21 along the extension direction D1 when the carrying device 20 rotates. In another embodiment, the first retaining element 242 is a retaining groove, and the second retaining element 34 is a ball spring plunger. Therefore, the cassette 30 is easily detached from or installed on the tray 21.

In the embodiment, the cassette 30 is a microfluidic cassette 30. As shown in FIG. 3, the body 31 of the cassette 30 has an injection groove 311, a number of capillary channels 312, and a number of storage grooves 313. The cassette 30 further includes a transparent cover 35 covering the injection grooves 311, the capillary channels 312, and the storage grooves 313 of the body 31. In addition, the transparent cover 35 is not illustrated in FIGS. 1 and 2. The transparent cover 35 has an injection hole 351 and an air hole 352. The injection hole 351 is in communication with the injection groove 311. The storage groove 313 is in communication with the injection groove 311 via the capillary channel 312. The storage groove 313 is a reaction groove or an overflow groove. The air hole 352 is in communication with one of the capillary channels 312.

A liquid specimen is injected into the injection groove 311 via the injection hole 351. When the rotation speed of the cassette 30 is high, the specimen in the injection groove 311 flows into the storage grooves 313 via the capillary channels 312. The air in the injection groove 311, the capillary channels 312, and/or the storage grooves 313 of the body 31 may be exhausted from the air hole 352 of the transparent cover 35.

The optical sensor device 40 is adjacent to the tray 21. The optical sensor device 40 is configured to detect the cassettes 30 and the positioning device 25. The optical sensor device 40 includes a signal generator 41 and a signal receiver 42 disposed at two opposite sides of the carrying device 20. The optical sensor device 40 further includes a stand 43. The signal generator 41 is disposed at the stand 43, and configured to generate a detection beam. The signal receiver 42 is disposed at the base 11, and configured to receive the detection beam generated by the signal generator 41. The signal generator 41 and the signal receiver 42 are located at an optical axis AX2, and the detection beam is transmitted along the optical axis AX2. In addition, the optical axis AX2 is parallel to the rotation axis AX1.

The stand 43 is fixed at the base 11. In another embodiment, the signal receiver 42 is disposed at the stand 43. In the embodiment, the stand 43 is to fix the positions of the signal generator 41 and/or the signal receiver 42. In another embodiment, the signal generator 41 and/or the signal receiver 42 may be fixed by other elements or other types of stand. For example, the stand 43 is fixed at the surface of a table, which the base 11 is disposed on. Therefore, the distances and the positions between the signal generator 41 and the signal receiver 42 of the optical sensor device 40, the rotation axis AX1, and the driving device 10 are fixed.

As shown in FIGS. 1 and 2, each of the storage grooves 313 corresponds to one of the detecting holes 234. The storage groove 313 and the detecting hole 234 are overlaid along the extension direction D1. The distances between the rotation axis AX1 and the optical axis AX2, the storage grooves 313, detecting holes 234, or the positioning device 25 are substantially the same. In other words, the storage grooves 313 and the detecting holes 234, and the positioning device 25 are located at a circular path. The tray 21 is located between the signal generator 41 and the signal receiver 42. In other words, the optical axis AX2 passes through the tray 21, and the detection beam falls on the tray 21.

Therefore, when the driving device 10 drives the carrying device 20 to rotate about a rotation axis AX1, the optical sensor device 40 detects the cassettes 30 and the positioning device 25 in sequence. At this time, the cassettes 30, the storage grooves 313 of the cassettes 30, the detecting holes 234, and the positioning device 25 pass through the optical axis AX2 and the detection beam in sequence. When the positioning device 25 passes through the optical axis AX2, the detection beam passes through the positioning device 25 and falls on the signal receiver 42. Moreover, the bottoms of the storage grooves 313 are made of transparent materials. Therefore, when the storage grooves 313 and the detecting holes 234 passes through the optical axis AX2, the detection beam falls on the signal receiver 42 via the storage grooves 313 and the detecting holes 234.

Figure 4:
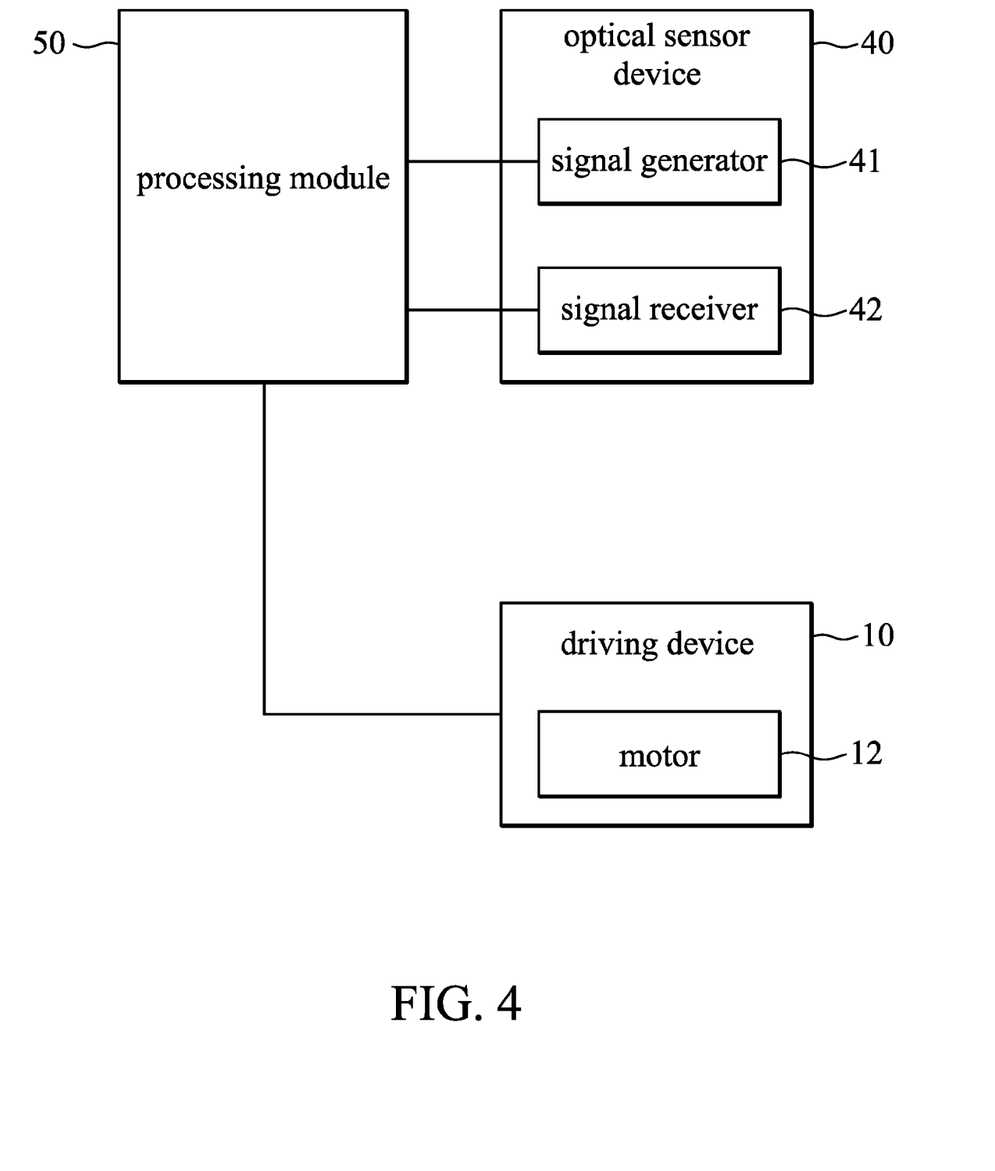
FIG. 4 is a system block diagram of the centrifugal analysis system in accordance with the first embodiment of the present disclosure.

FIG. 4 is a system block diagram of the centrifugal analysis system 1 in accordance with the first embodiment of the present disclosure. The centrifugal analysis system 1 further includes a processing module 50. The processing module 50 may be a computer. The processing module 50 is electrically connected with the signal generator 41, the signal receiver 42, and the motor 12. The processing module 50 is configured to drive the signal generator 41 and motor 12, and receives and processes the received signal from the signal receiver 42.

Figure 5:
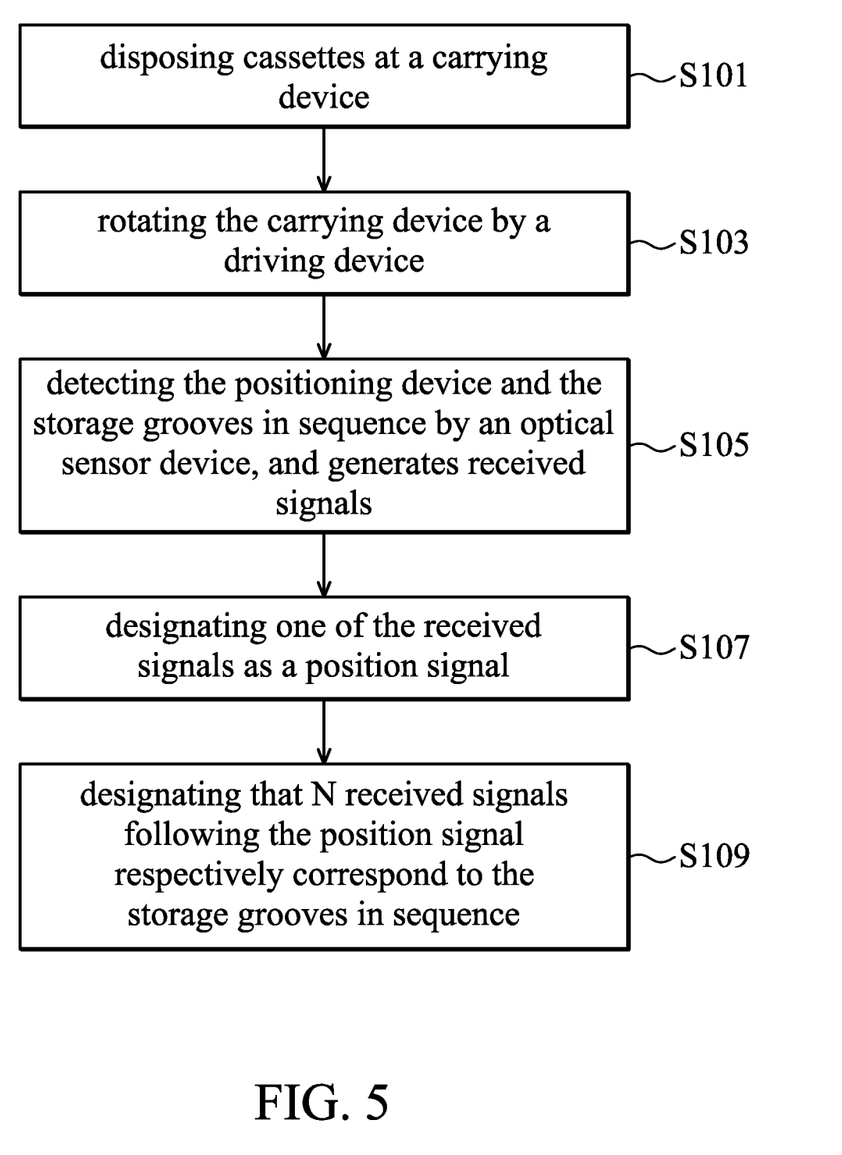
FIG. 5 is a flow chart of an analysis method in accordance with the first embodiment of the present disclosure.

FIG. 5 is a flow chart of an analysis method in accordance with the first embodiment of the present disclosure. In step S101, the cassettes 30 are disposed at the carrying device 20. For example, if there are many inspection items that need to be processed at the same time, a number of cassettes 30 can be disposed at the carrying device 20, and each of the cassettes 30 may correspond to different inspection items. Moreover, the specimens in the injection grooves 311 of different cassettes 30 may be different or the same. In the embodiments, there are three cassettes 30 and three limitation mechanisms 23. The cassettes 30 are respectively disposed at the limitation mechanisms 23. In addition, the number of cassettes 30 may be less than the number of limitation mechanisms 23. For example, only one or two cassettes 30 are disposed at the limitation mechanisms 23.

In step S103, the processing module 50 drives the motor 12 to make the driving device 10 rotate the carrying device 20, the cassettes 30 and the tray 21 about the rotation axis AX1 in the same direction.

In step S105, the optical sensor device 40 detects the positioning device 25 and the detecting holes 234 of the carrying device 20 and the storage grooves 313 of the cassettes 30 in sequence, and generates a number of received signals in sequence. In this step, the processing module 50 drives the signal generator 41 of the optical sensor device 40 to generate a detection beam, and the detection beam is transmitted toward the rotating tray 21.

When the positioning device 25 or the storage groove 313 passes through the optical sensor device 40 in sequence, the optical sensor device 40 generates received signals (position signals and inspection signals) in sequence. In other words, when the detection beam passes through the positioning device 25 or the storage grooves 313 and the detecting holes 234, and is received by the signal receiver 42, the signal receiver 42 generates a received signal, and transmits it to the processing module 50. The received signal may be a position signal or an inspection signal.

In the embodiment, since the tray 21 is continuously rotated, the detection beam passes through the positioning device 25 and the detecting holes 234 and storage grooves 313 in sequence, and the signal receiver 42 generates corresponding received signals.

In addition, by the rotation of the tray 21, the specimen flows into different storage grooves 313 via the capillary channels 312. When the detection beam passes through the storage grooves 313 having different volumes and/or components of the specimens, the optical characteristics, such as the spectrum of the detection beam, may change. Therefore, the inspection signals corresponding to different storage grooves 313 include the same or different values of optical parameters. The processing module 50 may analyze specimens in the storage grooves 313 according to the optical parameters of the inspection signals, and contain the parameter, such as a component or a physical property of the specimen in the storage groove corresponding to the inspection signal.

In step S107, one of the received signals is designated as a position signal by the processing module 50. The position signal is generated by the positioning device 25 and detected by the optical sensor device 40. For example, in the embodiment, the positioning device 25 is a positioning hole 25, and the area of the positioning hole 25 is greater than that of the detecting hole 234. The received signal further includes a set of strength information. The strength information is defined as the strength of the detection beam falling on the signal receiver 42.

Since the area of the positioning hole 25 is greater than the area of the detecting hole 234, the strength of the detection beam passing through the positioning hole 25 and falling on the signal receiver 42 is greater than the strength of the detection beam passing through the detecting hole 234 and falling on the signal receiver 42. Therefore, in the embodiment, when the strength information of the received signal complies with a determining condition, the received signal is determined as a position signal. For example, the determining condition is defined as the strength of the detection beam falling on the signal receiver 42 be a predetermined value or within a predetermined range.

Furthermore, since the spectrum of the detection beam passing through the positioning hole 25 is not changed by a specimen, the determining condition may be defined as whether the optical parameter, such as the color temperature or the wavelength, of the detection beam received by the signal receiver 42 corresponding to a predetermined value or within a predetermined range.

When the received signal complies with the determining condition, the processing module 50 determines the received signal complying with the determining condition as a position signal. When the received signal does not comply with the determining condition, the processing module 50 determines the received signal is an inspection signal.

In step S109, the processing module 50 designates N received signals following the position signal as inspection signals and respectively corresponding to the storage grooves 313 in sequence. The value N is a positive integer and corresponds to the number of the storage grooves 313.

For example, a first received signal received after the position signal is defined as a first inspection signal. A second received signal received after the position signal is defined as a second inspection signal. Moreover, as shown in FIG. 1, when the tray 21 is rotated, a first storage groove 313 irradiated by the detection beam after the positioning device 25 is defined as a first storage groove 313a of a first cassettes 30a. A second storage groove 313 irradiated by the detection beam after the positioning device 25 is defined as a second storage groove 313b of the first cassettes 30a. Therefore, the processing module 50 can easily make the first inspection signal corresponding to the first storage groove 313a, and the second inspection signal corresponding to the second storage groove 313b in accordance with the analysis method of the embodiment, and so on. Furthermore, the processing module 50 makes each of the inspection signals correspond to each of the storage grooves 313 of the cassettes 30.

Figure 6:
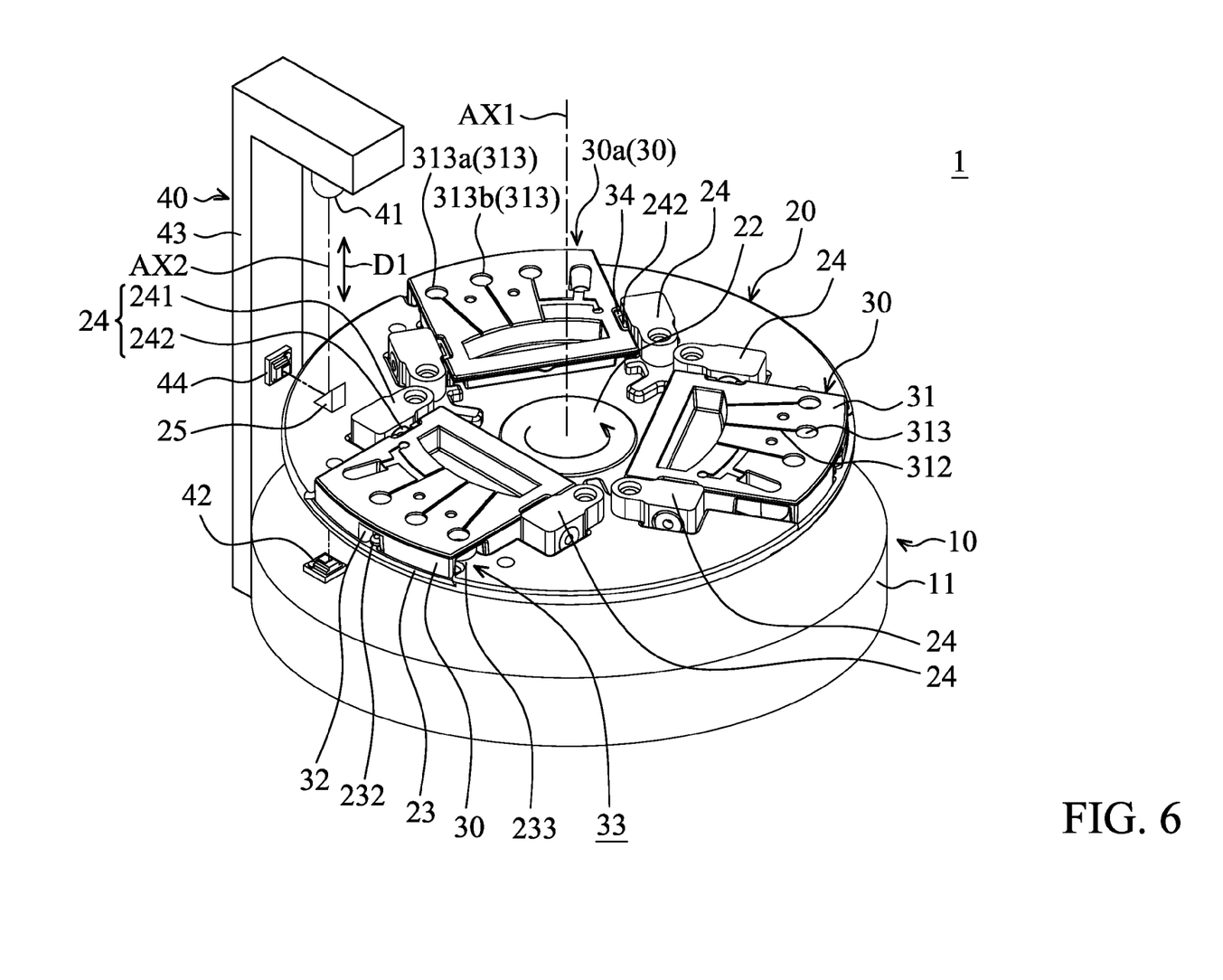
FIG. 6 is a perspective view of a centrifugal analysis system in accordance with a second embodiment of the present disclosure.
Figure 7:
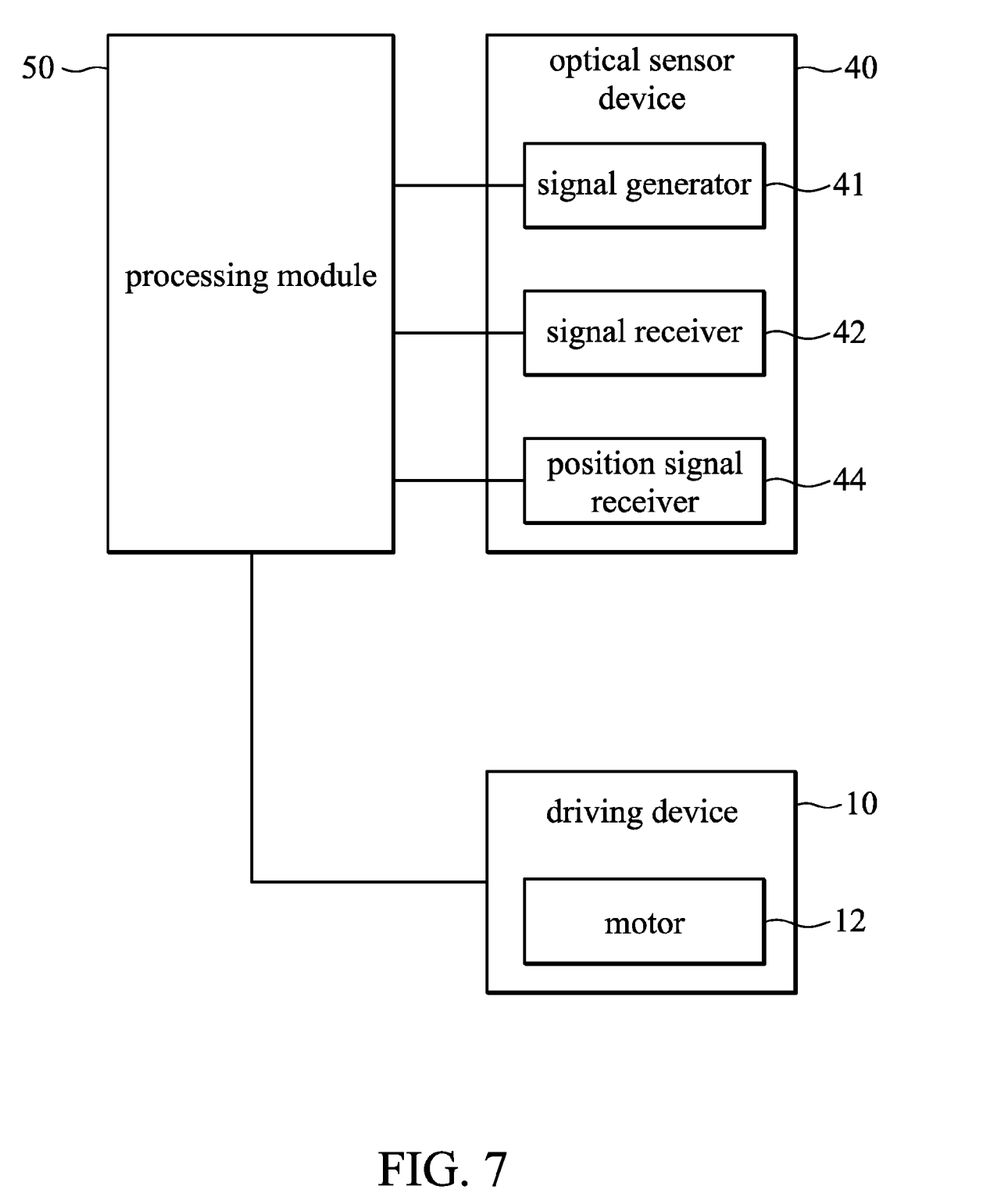
FIG. 7 is a system block diagram of the centrifugal analysis system in accordance with the second embodiment of the present disclosure.

FIG. 6 is a perspective view of the centrifugal analysis system 1 in accordance with a second embodiment of the present disclosure. FIG. 7 is a system block diagram of the centrifugal analysis system 1 in accordance with the second embodiment of the present disclosure. In the embodiment, the optical sensor device 40 further includes a position signal receiver 44. The position signal receiver 44 is disposed at the stand 43. The positioning device 25 may be a reflecting element 25, such as a reflecting mirror or a prism. When the reflecting element 25 passes through the detection beam, and the detection beam falls on the reflecting element 25, the reflecting element 25 reflects the detection beam to the position signal receiver 44.

In the embodiment, the signal receiver 42 is utilized to detect the detection beam passing through the detecting hole 234, and generate a corresponding inspection signal. The processing module 50 is electrically connected with the signal generator 42, and receives and processes the inspection signal transmitted by the signal receiver 42. Moreover, in the embodiment, the position signal receiver 44 is utilized to detect the detection beam passing through the positioning device 25, and generate a corresponding position signal. The processing module 50 is electrically connected with the position signal generator 44. The processing module 50 receives and processes the position signal, which received from the position signal receiver 44.

Figure 8:
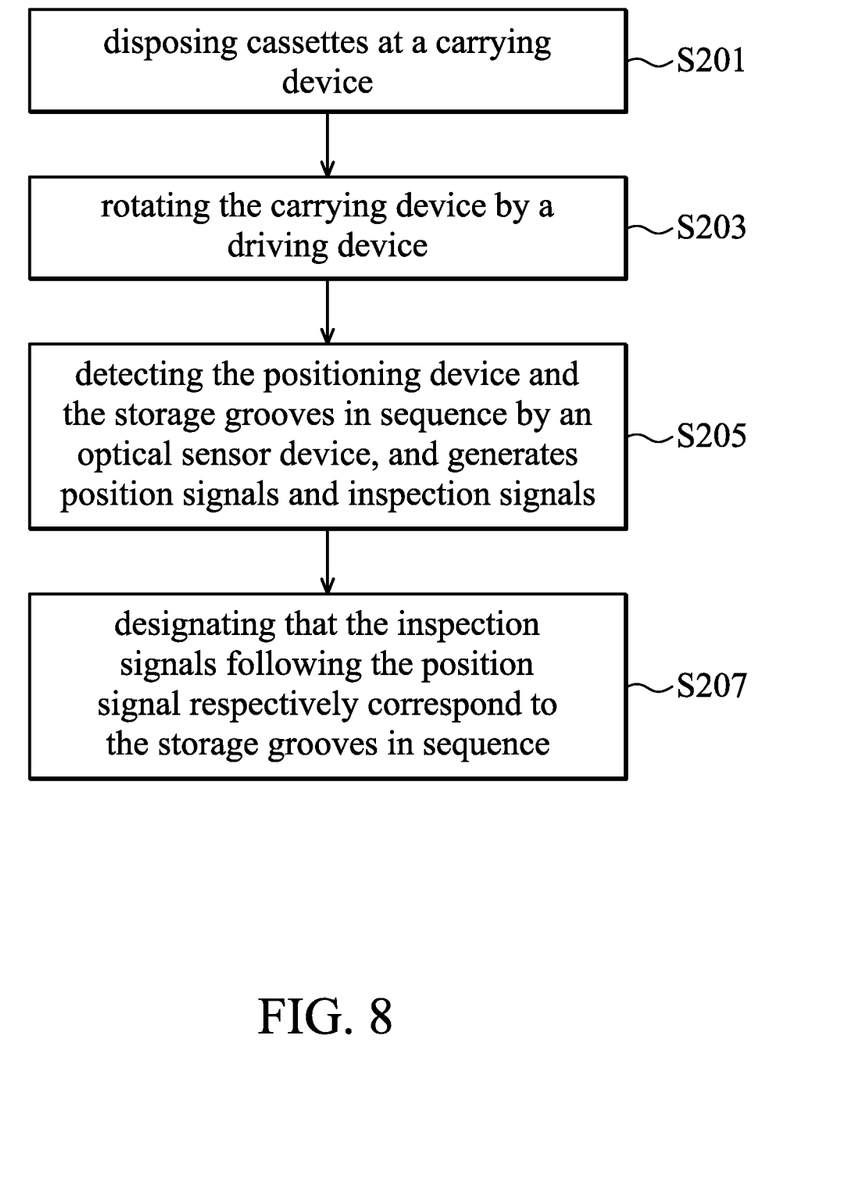
FIG. 8 is a flow chart of an analysis method in accordance with the second embodiment of the present disclosure.

FIG. 8 is a flow chart of an analysis method in accordance with the second embodiment of the present disclosure. In step S201, the cassettes 30 are disposed at the carrying device 20. In step S203, the processing module 50 drives the motor 12 to make the driving device 10 rotate the carrying device 20.

In step S205, the optical sensor device 40 detects the positioning device 25 and detecting holes 234 of the carrying device 20 and the storage grooves 313 of the cassettes 30, and generates corresponding position signals and inspection signals in sequence.

In step S207, in the embodiment, the signal receiver 42 is configured to generate the inspection signals, and the position signal receiver 44 is configured to generate the position signals. Therefore, the processing module 50 can easily designate that the inspection signals following the position signal respectively correspond to the storage grooves 313 in sequence after the processing module 50 receives the position signal from the position signal receiver 44.

In conclusion, the centrifugal analysis system of the present disclosure includes a number of cassettes with different specimens. The specimens can be inspected by a single inspection process at the same time. Moreover, the cassettes are detachably disposed at a carrying device via limitation mechanisms and/or retaining mechanisms.

While the invention has been described by way of example and in terms of preferred embodiment, it is to be understood that the invention is not limited thereto. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A centrifugal analysis system, comprising:
a driving device;
a carrying device, comprising a tray disposed at the driving device and a plurality of limitation mechanisms disposed at the tray;
a plurality of cassettes, detachably disposed at the tray, corresponding to the limitation mechanisms, and
an optical sensor device configured to generate a detection beam and detect the cassettes;
wherein when the driving device drives the carrying device to rotate, the optical sensor device detects the cassettes in sequence.

2. The centrifugal analysis system as claimed in claim 1, wherein the optical sensor device further comprises:
a signal generator configured to emit the detection beam; and
a signal receiver configured to receive the detection beam, wherein the tray is located between the signal generator and the signal receiver.

3. The centrifugal analysis system as claimed in claim 2, wherein the carrying device further comprises a positioning device, and when the positioning device passes through the detection beam, the detection beam falls on the signal receiver via the positioning device.

4. The centrifugal analysis system as claimed in claim 3, wherein the optical sensor device further comprises a position signal receiver, the positioning device is a reflecting element, and when the reflecting element passes through the detection beam, the reflecting element reflects the detection beam to the position signal receiver.

5. The centrifugal analysis system as claimed in claim 2, wherein each of the limitation mechanisms comprises at least one detecting hole, wherein when the detecting hole passes through the detection beam, the detection beam falls on the signal receiver via the detecting hole.

6. The centrifugal analysis system as claimed in claim 2, wherein each of the limitation mechanisms comprises at least one detecting hole, and each of the cassettes comprises a storage groove corresponding to the detecting hole, and when the storage groove and the detecting hole pass through the detection beam, the detection beam falls on the signal receiver via the storage groove and the detecting hole.

7. The centrifugal analysis system as claimed in claim 1, wherein the carrying device further comprises a positioning device, wherein the positioning device is a positioning hole passing through the tray, and each of the limitation mechanisms comprises at least one detecting hole, wherein an area of the positioning hole is different from an area of the detecting hole.

8. The centrifugal analysis system as claimed in claim 1, wherein each of the limitation mechanisms further comprises a receiving groove configured to receive one of the cassettes and a first fool-proofing mechanism is in the receiving groove, and each of the cassettes includes a second fool-proofing mechanism, wherein when the cassettes are disposed in the receiving grooves, the second fool-proofing mechanisms correspond to the first fool-proofing mechanisms.

9. The centrifugal analysis system as claimed in claim 1, further comprising a plurality of retaining mechanisms disposed at the tray, wherein when the cassettes are disposed at the limitation mechanisms, the retaining mechanisms clamp onto two opposite sides of each of the cassettes.

10. The centrifugal analysis system as claimed in claim 9, wherein each of the retaining mechanisms further includes a retaining body fixed at the tray, and a first retaining element disposed at the retaining body, and each of the cassettes further comprises a second retaining element, wherein when the cassettes are disposed at the limitation mechanisms, the first retaining element and the second retaining element are retained to each other.

11. An analysis method for a centrifugal analysis system, comprising:
disposing a plurality of cassettes at a carrying device, wherein each of the cassettes comprises at least one storage groove, and the carrying device comprises a positioning device and a plurality of detecting holes corresponding to the storage grooves;
rotating the carrying device by a driving device;
detecting the positioning device and the storage grooves in sequence by an optical sensor device, and generating a plurality of received signals in sequence;
designating one of the received signals as a position signal; and
designating that N received signals following the position signal respectively correspond to the storage grooves in sequence.

12. The analysis method as claimed in claim 11, further comprising determining the received signal complying with the determining condition as the position signal when one of the received signals complies with a determining condition.

13. The analysis method as claimed in claim 11, wherein the N is a positive integer, and the N corresponds to the number of the storage grooves.

14. An analysis method for a centrifugal analysis system, comprising:
disposing a plurality of cassettes at a carrying device, wherein each of the cassettes comprises a plurality of storage grooves, and the carrying device comprises a positioning device and a plurality of detecting holes corresponding to the storage grooves;
rotating the carrying device by a driving device;
detecting the positioning device and the storage grooves in sequence by an optical sensor device, and generating a position signal and a plurality of inspection signals in sequence; and
designating that the inspection signals following the position signal respectively correspond to the storage grooves in sequence.

15. The analysis method as claimed in claim 14, wherein the storage grooves are configured to receive a specimen, wherein the analysis method further comprises: analyzing the inspection signal to contain the parameter of a component or a physical property of the specimen in one of the storage grooves corresponding to the inspection signal.

* * * * *